United States Patent
Wagner

(10) Patent No.: US 9,682,280 B1
(45) Date of Patent: Jun. 20, 2017

(54) SYSTEM FOR ANALYSING ATHLETIC MOVEMENT

(71) Applicant: SPARTA SOFTWARE CORPORATION, Menlo Park, CA (US)

(72) Inventor: Phillip Patrick Wagner, Menlo Park, CA (US)

(73) Assignee: SPARTA SOFTWARE CORPORATION, Menlo Park, CA (US)

( * ) Notice: Subject to any disclaimer, the term of this patent is extended or adjusted under 35 U.S.C. 154(b) by 308 days.

(21) Appl. No.: 14/033,259

(22) Filed: Sep. 20, 2013

(51) Int. Cl.
  *A63B 24/00* (2006.01)

(52) U.S. Cl.
  CPC ................ *A63B 24/0062* (2013.01)

(58) Field of Classification Search
  CPC ....... G01L 25/00; G01L 5/161; A61B 5/1036; A61B 5/1112; A61B 5/11; A61B 2503/10; A63B 2220/51; A63B 2220/806; A63B 2225/50; A63B 22/0235; A63B 24/0062; A63B 71/06; A63B 2220/803; A63B 24/0021; A63B 69/0028; A63B 2024/0065; A63B 24/003; A63B 5/00; A63B 2024/0009; G06T 7/20
  See application file for complete search history.

(56) References Cited

U.S. PATENT DOCUMENTS

| | | | | |
|---|---|---|---|---|
| 6,539,327 | B1 * | 3/2003 | Dassot | G01V 3/081 702/150 |
| 6,786,730 | B2 * | 9/2004 | Bleckley | A63B 24/0003 434/247 |
| 7,530,925 | B2 * | 5/2009 | Underwood | 482/15 |
| 7,670,263 | B2 * | 3/2010 | Ellis | A61B 5/1038 342/357.75 |
| 8,315,822 | B2 * | 11/2012 | Berme et al. | 702/41 |
| 8,315,823 | B2 * | 11/2012 | Berme et al. | 702/41 |
| 8,544,347 | B1 * | 10/2013 | Berme | 73/862.041 |
| 8,858,400 | B2 * | 10/2014 | Johnson | A63B 24/0075 482/1 |
| 8,915,149 | B1 * | 12/2014 | Berme | 73/862.041 |
| 2009/0023557 | A1 * | 1/2009 | Underwood | 482/15 |
| 2009/0030350 | A1 * | 1/2009 | Yang | A61B 5/1038 600/595 |
| 2009/0062627 | A1 * | 3/2009 | Younger | A63B 24/0003 600/301 |
| 2009/0069722 | A1 * | 3/2009 | Flaction | G06K 9/00342 600/587 |

(Continued)

OTHER PUBLICATIONS

U.S. Appl. No. 61/818,776 to Rolley, published as U.S. pre-grant publication 2014/0330408 A1.*

(Continued)

*Primary Examiner* — David L Lewis
*Assistant Examiner* — Matthew D. Hoel
(74) *Attorney, Agent, or Firm* — One LLP

(57) ABSTRACT

A system for analyzing athletic performance is disclosed. The system includes at least one sensor for sensing an aspect of an athletic movement for an athlete that varies during said movement an to generate sensor data corresponding thereto; and a processor for executing instructions to extract portions of the sensor data corresponding to a load phase, an explode phase, and a drive phase of the athletic movement.

6 Claims, 3 Drawing Sheets

(56) References Cited

U.S. PATENT DOCUMENTS

| | | | | |
|---|---|---|---|---|
| 2009/0210078 A1* | 8/2009 | Crowley | ............... | G06Q 30/02 700/91 |
| 2010/0173732 A1* | 7/2010 | Vaniche | ............ | A63B 24/0003 473/422 |
| 2010/0317489 A1* | 12/2010 | Flaction | ................... | A61B 5/11 482/9 |
| 2012/0023163 A1* | 1/2012 | Mangold | ............... | A63B 69/00 709/203 |
| 2012/0029666 A1* | 2/2012 | Crowley | ............ | A63B 24/0062 700/91 |
| 2012/0071733 A1* | 3/2012 | Grey | .................. | G06F 19/3481 600/301 |
| 2012/0212505 A1* | 8/2012 | Burroughs | ......... | G09B 19/0038 345/629 |
| 2013/0079907 A1* | 3/2013 | Homsi | .................. | A63B 24/00 700/91 |
| 2013/0252216 A1* | 9/2013 | Clavin | ............... | G09B 19/0038 434/257 |
| 2014/0074179 A1* | 3/2014 | Heldman | ............ | A61B 5/1101 607/45 |
| 2014/0074265 A1* | 3/2014 | Arginsky | ........... | A63B 71/0622 700/91 |
| 2014/0180173 A1* | 6/2014 | Sullivan | ................ | A61B 5/112 600/595 |
| 2014/0287391 A1* | 9/2014 | Krull | ..................... | A63B 69/00 434/247 |
| 2014/0330408 A1* | 11/2014 | Rolley | ............................ | 700/91 |
| 2014/0336796 A1* | 11/2014 | Agnew | ............... | A43B 3/0005 700/91 |
| 2015/0154403 A1* | 6/2015 | Dornbush | ............. | A63B 71/06 700/91 |

OTHER PUBLICATIONS

"Dynamics of Vertical Jumps," by Psycharakis.*
"Mechanics of the Vertical Jump and Two-Joint Muscles: Implications for Training," by Umberger, Strength and Conditioning, Oct. 1998.*
"Analysis of Standing Vertical Jumps Using a Force Platform," by Lithorne, Am. J. Phys., 69 (11), Nov. 2001.*
"Coaches' Guide to Sports Injuries," Randolph Hospital, Dec. 18, 2010.*
"Clinical Practice Guide for Muscular Injuries. Epidemiology, Diagnosis, Treatment and Prevention," Medical Services, Futbol Club Barcelona, Feb. 9, 2009.*
"Net Impulse and Net Impulse Characteristics in Vertical Jumping," Satoshi Mizuguchi, 2012.*

* cited by examiner

SYSTEM FOR ANALYSING ATHLETIC MOVEMENT

FIELD

Embodiments of the present invention relate to athletic performance. In particular, embodiments of the present invention relate to systems for analyzing athletic movement

BACKGROUND

A force plate may be used to generate data relating to athletic movement, e.g. in the form of a jump. However, the data can be quite voluminous as a data point may be generated once every millisecond. This makes analysis of the data difficult.

SUMMARY

According to a first aspect of the invention, there is provided a system for analyzing athlete movement data. The system comprises at least one sensor to generate data during the athletic movement. The sensor may be a force-plate configured to generate force-time data corresponding to an athletic movement in the form of a vertical jump. The data is the processed to extract load, explode, and drive phase data corresponding the jump to produce an athletic signature.

Other aspects of the invention will be apparent from the detailed description below.

DETAILED DESCRIPTION

In the following description, for purposes of explanation, numerous specific details are set forth in order to provide a thorough understanding of the invention. It will be apparent, however, to one skilled in the art that the invention can be practiced without these specific details. In other instances, structures and devices are shown in block or flow diagram form only in order to avoid obscuring the invention.

Reference in this specification to "one embodiment" or "an embodiment" means that a particular feature, structure, or characteristic described in connection with the embodiment is included in at least one embodiment of the invention. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Moreover, although the following description contains many specifics for the purposes of illustration, anyone skilled in the art will appreciate that many variations and/or alterations to the details are within the scope of the present invention. Similarly, although many of the features of the present invention are described in terms of each other, or in conjunction with each other, one skilled in the art will appreciate that many of these features can be provided independently of other features. Accordingly, this description of the invention is set forth without any loss of generality to, and without imposing limitations upon, the invention.

Figure 1:
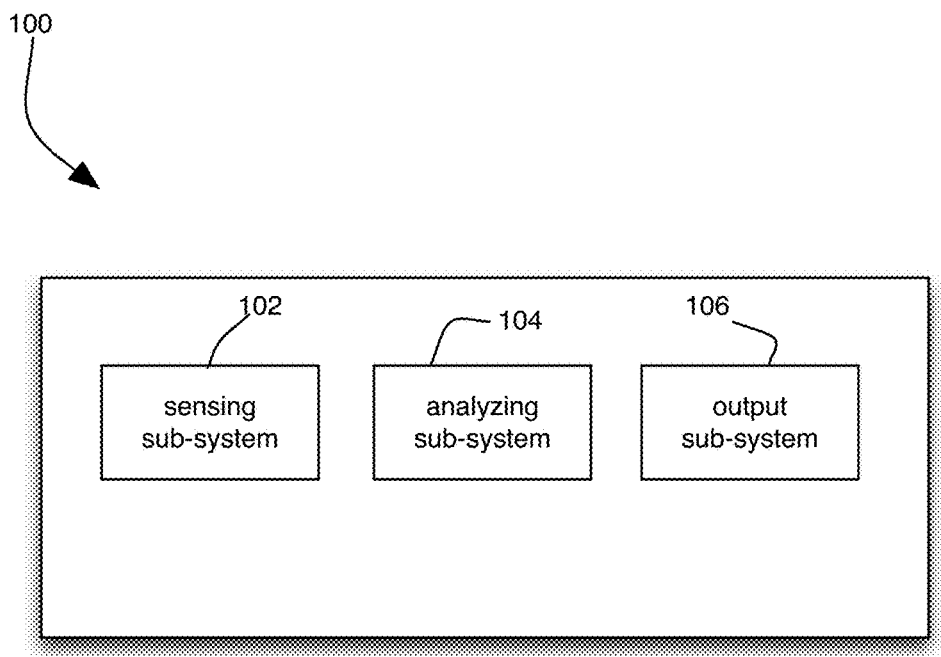
FIG. 1 shows a logical block diagram of a system to analyze athletic movement, in accordance with one embodiment of the invention.

Referring to FIG. 1, embodiments of the present invention disclose a system 100 for analyzing athletic movement. For illustrative purposes consider the athletic movement to be a vertical jump. However, it is to be understood that at the system maybe used to analyze other forms of athletic movement, such as golf and baseball swings, baseball and football throws, sprinting, agility, basketball shooting, and kicking.

The system 100 may, at least logically, be divided into a sensing sub-system 102, an analytical sub-system 104, and an output sub-system 106.

Figure 2:
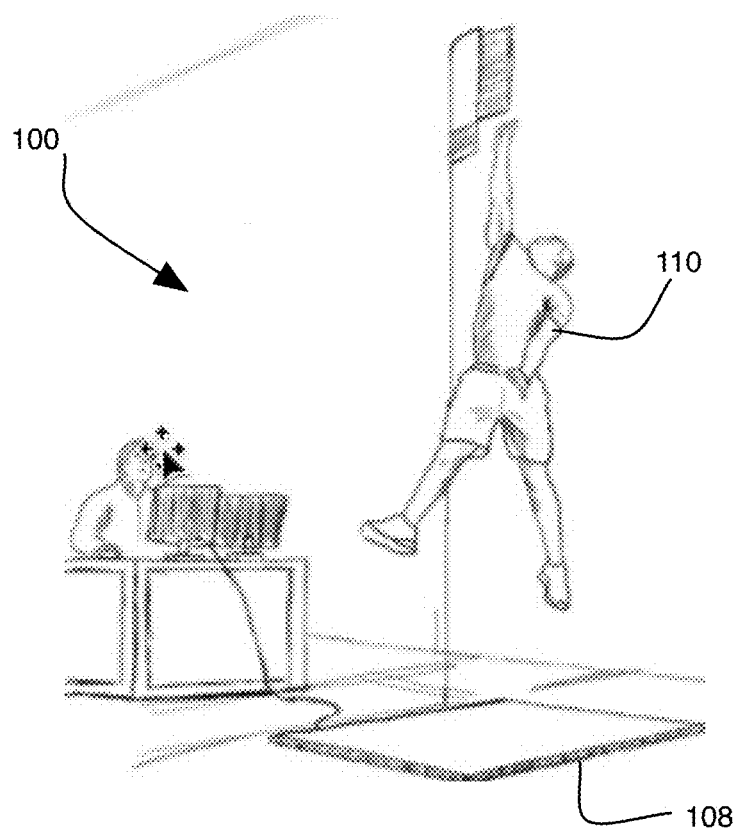
FIG. 2 shows the system of FIG. 1 implemented with a force-plate, in accordance with one embodiment of the invention

The sensing sub-system 102 may include sensors for sensing a time-dependent variable that changes during the athletic movement. In one embodiment, the sensing sub-system 102 may include a sensor in the form of a force-plate 108, as shown in FIG. 2. In other embodiments, the sensing sub-system 102 may include other types of sensors. For example, in one embodiment, the sensing sub-system 102 may include an accelerometer, which may be integrated, for example, into a bracelet or a shoe pod. In use, an athlete 110 initiates a vertical jump (athletic movement) on the force-plate 108. The force plate records changes in force over time (typically one force reading in captured each millisecond). An analog-to-digital converter (not shown) converts the analog force signal into a digital signal for analysis by the analytical sub-system 104.

The analytical sub-system 104 may include instructions to process the digital signal in order to compile an athletic signature for the athlete 110. In one embodiment, the analytical sub-system 104 extracts selected portions of a force-time curve output by the sensing sub-system 102. Said selected portions may comprise phases of the jump including a load phase, an explode phase, and a drive phase, as detailed below:

(a) load phase: comprises data relating to the average eccentric rate of force development during the jump.

(b) explode phase: comprises data relating to the average relative concentric peak force generated during the jump, computed as average concentric peak force divide by the athlete's weight.

(c) drive phase: comprises data relating to the concentric relative impulse for the jump.

Typically, the system 100 is configured to process a plurality of jumps for each athlete and to store data for each athlete in the form of an athletic signature Each athletic signature may by used to profile an athlete in terms of at least suitability for a given sport, proneness to injury, suitability for particular athletic gear (e.g. shoes), etc.

The output sub-system 106 facilitates output of athletic signatures via printout, display, etc.

Figure 3:
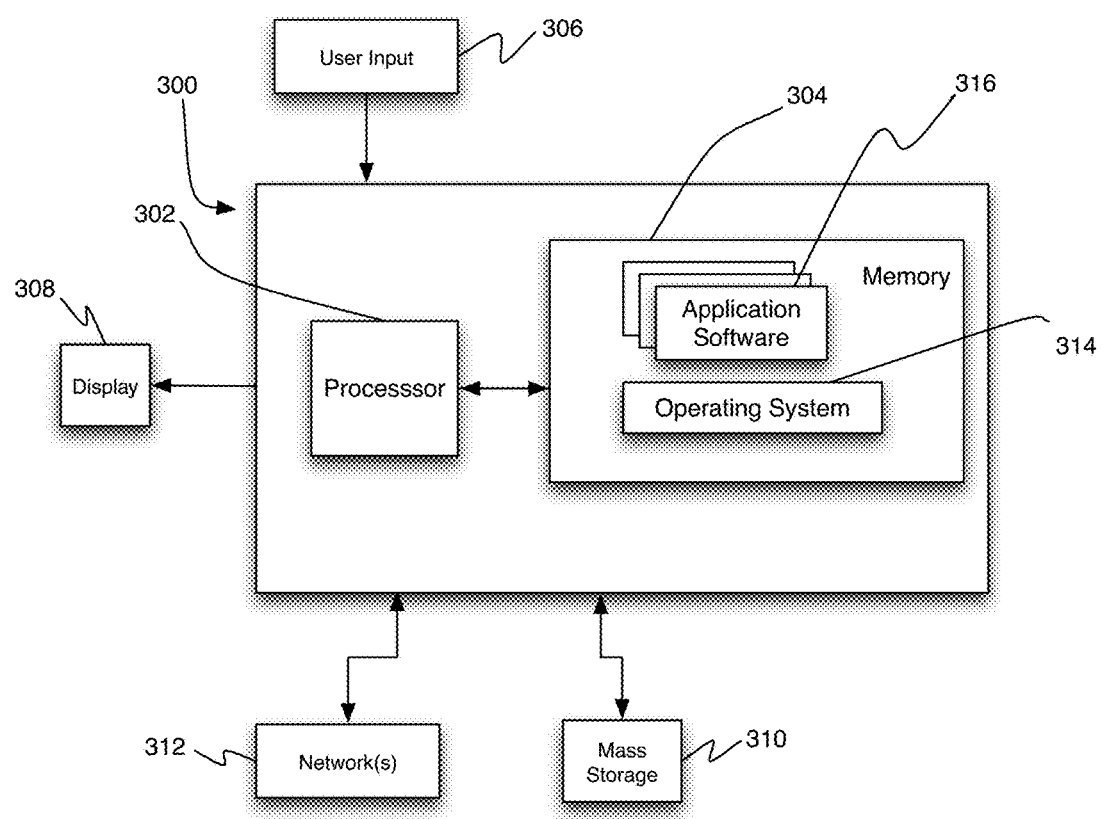
FIG. 3 shows a high-level block diagram of hardware used to implement the system of FIG. 1, in accordance with one embodiment of the invention.

FIG. 3 shows an example of hardware 300 that may be used to implement portions of the system 300, in accordance with one embodiment. The hardware 300 may includes at least one processor 302 coupled to a memory 304. The processor 303 may represent one or more processors (e.g., microprocessors), and the memory 304 may represent random access memory (RAM) devices comprising a main storage of the hardware, as well as any supplemental levels of memory e.g., cache memories, non-volatile or back-up memories (e.g. programmable or flash memories), read-only memories, etc. In addition, the memory 304 may be considered to include memory storage physically located elsewhere in the hardware, e.g. any cache memory in the processor 302, as well as any storage capacity used as a virtual memory, e.g., as stored on a mass storage device.

The hardware also typically receives a number of inputs and outputs for communicating information externally. For interface with a user or operator, the hardware may include one or more user input/output devices 306 (e.g., force-plate, keyboard, mouse, etc.) and a display 308. For additional storage, the hardware 300 may also include one or more mass storage devices 310, e.g., a Universal Serial Bus (USB) or other removable disk drive, a hard disk drive, a Direct Access Storage Device (DASD), an optical drive (e.g. a Compact Disk (CD) drive, a Digital Versatile Disk (DVD) drive, etc.) and/or a USB drive, among others. Furthermore, the hardware may include an interface with one or more networks 312 (e.g., a local area network (LAN), a wide area network (WAN), a wireless network, and/or the Internet among others) to permit the communication of information with other computers coupled to the networks. It should be appreciated that the hardware typically includes suitable analog and/or digital interfaces between the processor 312 and each of the components, as is well known in the art.

The hardware 300 operates under the control of an operating system 314, and executes application software 316 which includes various computer software applications, components, programs, objects, modules, etc. to perform the techniques described above.

In general, the routines executed to implement the embodiments of the invention, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processors in a computer, cause the computer to perform operations necessary to execute elements involving the various aspects of the invention. Moreover, while the invention has been described in the context of fully functioning computers and computer systems, those skilled in the art will appreciate that the various embodiments of the invention are capable of being distributed as a program product in a variety of forms, and that the invention applies equally regardless of the particular type of machine or computer-readable media used to actually effect the distribution. Examples of computer-readable media include but are not limited to recordable type media such as volatile and non-volatile memory devices, USB and other removable media, hard disk drives, optical disks (e.g., Compact Disk Read-Only Memory (CD ROMS), Digital Versatile Disks, (DVDs), etc.), flash drives among others.

Although the present invention has been described with reference to specific exemplary embodiments, it will be evident that the various modification and changes can be made to these embodiments without departing from the broader spirit of the invention. Accordingly, the specification and drawings are to be regarded in an illustrative sense rather than in a restrictive sense.

The invention claimed is:

1. A system, comprising:
a sensing sub-system, comprising:
at least one sensor for sensing an aspect of an athletic movement for an athlete, wherein the aspect of the athletic movement varies as a function of time during the athletic movement to generate an analog sensor signal; and
an analog-to-digital converter coupled to the at least one sensor, the analog-to-digital converter configured to convert the analog sensor signal into a first digital sensor signal and to communicate the first digital sensor signal to an analytical sub-system; and
the analytical sub-system comprising:
one or more processors;
a memory coupled to the one or more processors, the memory storing instructions that, when executed by the one or more processors, cause the one or more processors to:
extract a plurality of portions of the first digital sensor signal upon receipt, the plurality of extracted portions including: a load phase measurement comprising an average eccentric rate of force development during the athletic movement; an explode phase measurement comprising an average relative concentric force during the athletic movement divided by a weight of the athlete; and a drive phase measurement comprising a concentric relative impulse during the athletic movement;
store the plurality of extracted portions to a mass storage device as an athletic signature associated with the athlete; and
generate, by the one or more processors, a profile of the athlete based on the stored athletic signature of the athlete, wherein the profile of the athlete is expressed as at least one of a plurality of profile parameters, including suitability for a given sport, proneness to injury, and suitability for particular athletic gear, and wherein each profile parameter is associated with an archetypal combination of a load phase measurement, an explode phase measurement and a drive phase measurement.

2. The system of claim 1, wherein the at least one sensor comprises a force-plate.

3. The system of claim 1, wherein the athletic movement comprises a vertical jump.

4. The system of claim 1, further comprising an output sub-system including a display for visually outputting the athletic signature of the athlete.

5. The system of claim 1, wherein the at least one sensor comprises an accelerometer integrated into a wearable device comprising a shoe or a bracelet.

6. The system of claim 1, wherein the memory of the analytical sub-system stores instructions that, when executed by the one or more processors, further cause the one or more processors to extract a plurality of portions of a second digital sensor signal, and update the profile of the athlete based on the plurality of extracted portions of the second digital sensor signal.

* * * * *